United States Patent [19]
Otake et al.

[11] Patent Number: 4,565,781
[45] Date of Patent: Jan. 21, 1986

[54] ANTIBIOTIC, SPICAMYCIN

[75] Inventors: Noboru Ōtake, Yokohama; Yoichi Hayakawa, Tokyo; Hiroyuki Kawai, Urawa; Masaya Nakagawa, Ichikawa; Kozo Tanabe; Junichiro Mochizuki, both of Takasaki, all of Japan

[73] Assignee: Kirin Beer Kabushiki Kaisha, Tokyo, Japan

[21] Appl. No.: 583,108

[22] Filed: Feb. 24, 1984

[30] Foreign Application Priority Data

Mar. 4, 1983 [JP] Japan ................................. 58-35662

[51] Int. Cl.$^4$ .................. C12P 19/40; C12P 19/28; C07H 17/02; C07H 19/06
[52] U.S. Cl. .......................................... 435/88; 536/22; 536/24; 536/26; 424/119; 435/85; 435/87
[58] Field of Search ..................... 536/22, 24, 26; 424/119; 435/85, 87, 88

[56] References Cited

U.S. PATENT DOCUMENTS 3,155,647 11/1964 Dutcher .
3,264,195 8/1966 Dutcher et al. ...................... 536/24
4,086,416 4/1978 Acton et al. ......................... 536/24

OTHER PUBLICATIONS

Chemical Abstracts, vol. 99, Abstract No. 118916a, 1983.
H. Agahigian, G. D. Vickers, M. H. von Saltza, Joyce Reid, A. I. Cohen and H. Gauthier, J. Organic Chemistry, "Nuclear Magnetic Resonance Spectroscopy of Acetylated Methyl Glycopyranosides of Aminohexoses. Characterization of an Aminohexose from Septacidin", p. 1085 (1965).

*Primary Examiner*—Blondel Hazel

*Attorney, Agent, or Firm*—Ladas & Parry

[57] ABSTRACT

An antibiotic, Spicamycin, having the physicochemical properties set forth below is produced by aerobically cultivating a Spicamycin-producing Streptomyces strain in a suitable culture medium, and recovering from the culture the antibiotic, Spicamycin.

(1) Color and properties: Weakly acidic white powder
(2) Melting point: 215° to 220° C. (decomposed)
(3) Specific rotatory power: $[\alpha]_D^{25} = +15°$ (C: 0.15, in methanol)
(4) Elementary analysis (Found): C: 57.4%, H: 8.3%; N: 15.7%, O: 18.6%
(5) Ultraviolet absorption spectrum (maximum):

| | |
|---|---|
| CH$_3$OH | 264 nm (E$_{1cm}^{1\%}$ 257) |
| 0.01N NaOH + CH$_3$OH | 272 nm (E$_{1cm}^{1\%}$ 226) |
| 0.01N HCl + CH$_3$OH | 273 nm (E$_{1cm}^{1\%}$ 258) |

(6) Infrared absorption spectrum (as measured by the potassium bromide method): As shown in FIG. 2.
(7) Solubility in Solvent: Soluble in basic water, dimethyl sulfoxide, methanol, ethanol, n-propanol, and n-butanol. Sparingly soluble in water, acetone, ethyl acetate, and chloroform. Insoluble in benzene, ethyl ether, and hexane.
(8) Thin layer chromatography (using "Silica Gel 60F$_{254}$" plate supplied by Merck & Co., Inc.):

| Developing solvent | Rf value |
|---|---|
| Chloroform:Methanol (1:1) | 0.34 |

(9) NMR spectrum (400 MHz, in deuteromethanol): As shown in FIG. 3.

2 Claims, 3 Drawing Figures

ANTIBIOTIC, SPICAMYCIN

BACKGROUND OF THE INVENTION

The present invention relates to a novel carcinostatic antibiotic and a process for the production thereof.

Carcinostatic antibiotics assume an important position in medicine, and various species of such antibiotics have been proposed so far.

Generally, the physiological activities of antibiotics depend greatly on the chemical structures or physicochemical properties of the chemical substances constituting the antibiotics, and there has been a continual search for antibiotics of a great variety of characteristics. There has been a constant demand, therefore, also for carcinostatic antibiotics composed of chemical substances which differ from conventional ones or possessing physicochemical properties which differ from those of known antibiotics.

SUMMARY OF THE INVENTION

The present invention meets the above-mentioned demand.

More particularly, this invention provides an antibiotic, Spicamycin, having the physicochemical properties set forth below.

This invention also provides a process for producing the antibiotic, Spicamycin, which process comprises aerobically cultivating a Spicamycin-producing Streptomyces strain in a suitable culture medium, and recovering from the culture the antibiotic, Spicamycin, having the following physicochemical properties.

(1) Color and properties: Weakly acidic white powder
(2) Melting point: 215° to 220° C. (decomposed)
(3) Specific rotatory power: $[\alpha]_D^{25} = +15°$ (C: 0.15, in methanol)
(4) Elementary analysis (Found): C: 57.4%, H: 8.3%; N: 15.7%, O: 18.6%.
(5) Ultraviolet absorption spectrum (maximum):

| | |
|---|---|
| CH$_3$OH | 264 nm (E$_{1cm}^{1\%}$ 257) |
| 0.01N NaOH + CH$_3$OH | 272 nm (E$_{1cm}^{1\%}$ 226) |
| 0.01N HCl + CH$_3$OH | 273 nm (E$_{1cm}^{1\%}$ 258) |

(6) Infrared absorption spectrum (as measured by the potassium bromide method): As shown in FIG. 2.
(7) Solubility in solvent: Soluble in basic water, dimethyl sulfoxide, methanol, ethanol, n-propanol, and n-butanol. Sparingly soluble in water, acetone, ethyl acetate, and chloroform. Insoluble in benzene, ethyl ether, and hexane.
(8) Thin layer chromatography (using "Silica Gel 60F$_{254}$" plate supplied by Merck & Co., Inc.):

| Developing solvent | Rf value |
|---|---|
| Chloroform:Methanol (1:1) | 0.34 |

(9) NMR spectrum (400 MHz, in deuteromethanol): As shown in FIG. 3.

DETAILED DESCRIPTION OF THE INVENTION

Antibiotic, Spicamycin

Chemical structure

Figure 1:
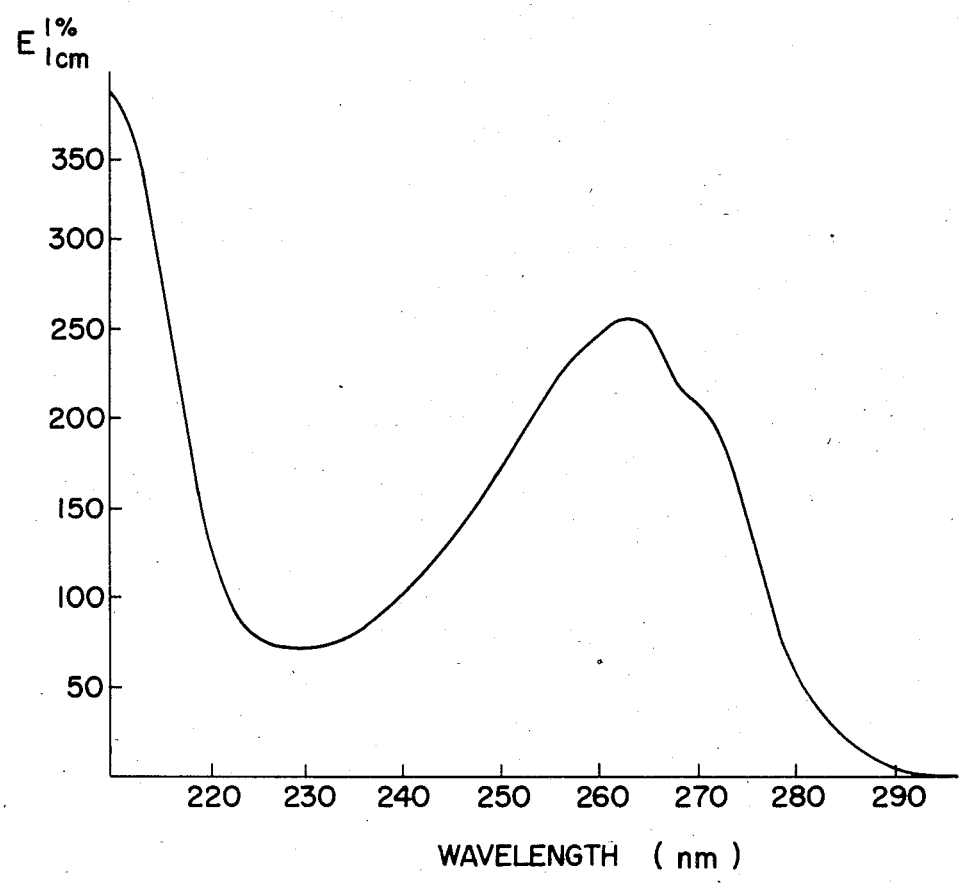
FIG. 1 is the ultraviolet absorption spectrum of Spicamycin (in methanol)

The antibiotic, Spicamycin, according to the present invention is a mixture of compounds represented by the following formula (I):

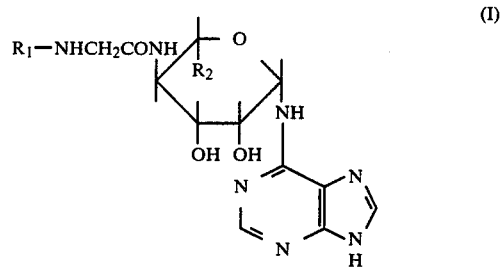

(I)

wherein R$_1$ is (CH$_3$)$_2$CH(CH$_2$)$_n$CO— (n=8-14) or CH$_3$(CH$_2$)$_m$CO— (m=10-16), and R$_2$ is CH$_2$(OH)CH(OH)—.

The chemical structure of Spicamycin shown above was determined as follows.

Upon analysis of the NMR spectrum of Spicamycin (FIG. 3), it can be presumed that this antibiotic comprises an iso-type fatty acid moiety, a heptose moiety, a heteroaromatic moiety, and a moiety containing methylene (classification unidentified).

By hydrolyzing Spicamycin in an aqueous solution of 1N HCl at 100° C. for one hour, adenine, an unknown amino sugar, and an acidic substance can be obtained. By further hydrolyzing this acidic substance in an aqueous solution of 6N HCl at 110° C. for 48 hours, glycine and a mixture of saturated fatty acids can be obtained. The mixture of saturated fatty acids thus obtained was methylated with diazomethane and analyzed by means of gas chromatography-mass spectrometry (1.5% Silicone-OV-1/Shimalite W 170° C.), whereupon this mixture was found to comprise fatty acids represented by (CH$_3$)$_2$CH(CH$_2$)$_n$COOH (n=8-14) or CH$_3$(CH$_2$)$_m$COOH (m=10-16), typically iso-palmitic acid and isomargaric acid.

As a result, the heptose, heteroaromatic and methylene moieties of Spicamycin as determined by the NMR spectrum can be identified respectively as aminoheptose, adenine and glycine. The above results also suggest that the fatty acid is bound to the glycine through amide linkage.

Further, Spicamycin is acetylated with acetic anhydride in pyridine in the presence of 4-dimethylaminopyridine to analyze the sugar moiety, whereby Spicamycin tetraacetate is obtained. Upon analysis of the NMR spectrum ($^1$H-NMR) of the Spicamycin tetraacetate to determine the structure thereof, coupling of the proton of the amino group at the 6-position of the adenine with the protons at the 1'-to 7'-positions of the heptose was observed, and hence the aminoheptose of Spicamycin was found to be bound to the amino group at the 6-position of the adenine through N-glycoside linkage. Also in view of the fact that the coupling constant between the 5'-position and 4'-position and that between the 4'-position and 3'-position were each about 10 Hz while that between the 3'-position and 2'-position was about 3 Hz, the proton at the 2'-position was found to be equatorial, and all of the protons at the 3'-position to 5'-position were found to be axial.

Further in view of the fact that no shift of acetyl groups was observed at the 4'-position and 5'-position while coupling was observed between the proton at the 4'-position and the proton bound to N, the sugar was found to be of pyranose type, in which sugar N-acylglycine was bound to its 4'-position through amide linkage. Furthermore, NOE (nuclear Overhauser effect) was observed between the proton at the 1'position and those at the 2'-, 3'- and 5'-positions, so that the proton at the 1'-position of the sugar was found to be axially oriented.

As an overall result, Spicamycin was identified as a mixture of compounds represented by the formula (I) indicated hereinbefore.

The FD-mass spectrum of Spicamycin reached peaks at m/z 644, 658 and 672 (M+ +Na) which designate the molecular ion peaks of the compounds of the formula (I) wherein $R_1$ is $(CH_3)_2CH(CH_2)_nCO-$ (n=12-14) or $CH_3(CH_2)_mCO-$ (m=14-16).

Physicochemical properties

The physicochemical properties of the antibiotic, Spicamycin, are as follows.

(1) Color and properties: Weakly acidic white powder
(2) Melting point: 215° to 220° C. (decomposed)
(3) Specific rotatory power: $[\alpha]_D^{25} = +15°$ (C: 0.15, in methanol)
(4) Elementary analysis (Found): C: 57.4%, H: 8.3%;. N: 15.7%, O: 18.6%
(5) Ultraviolet absorption spectrum (maximum):

| | |
|---|---|
| $CH_3OH$ | 264 nm ($E_{1cm}^{1\%}$ 257) |
| 0.01N NaOH + $CH_3OH$ | 272 nm ($E_{1cm}^{1\%}$ 226) |
| 0.01N HCl + $CH_3OH$ | 273 nm ($E_{1cm}^{1\%}$ 258) |

Figure 2:
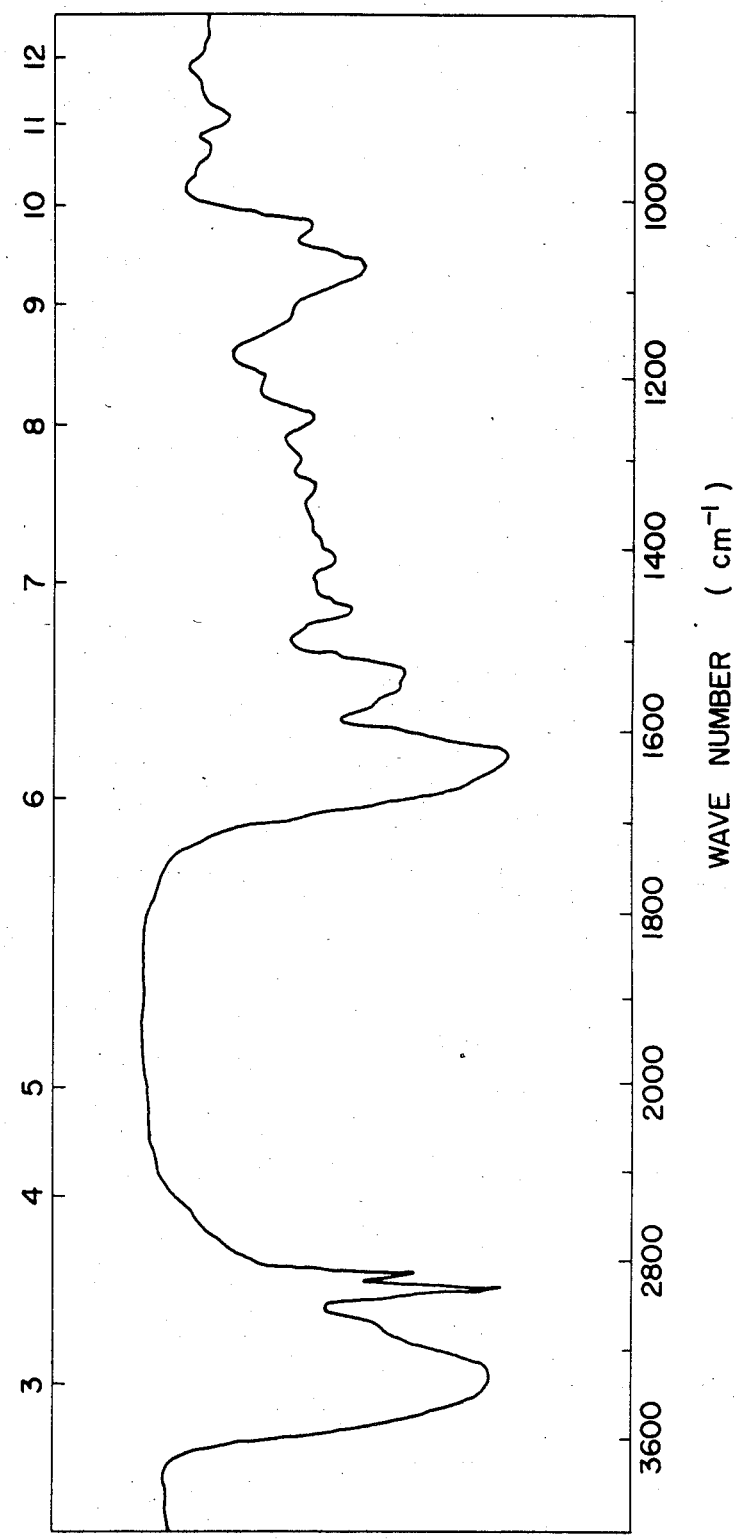
FIG. 2 is the infrared absorption spectrum of Spicamycin.

(6) Infrared absorption spectrum (as measured by the potassium bromide method): As shown in FIG. 2.
(7) Solubility in solvent: Soluble in basic water, dimethyl sulfoxide, methanol, ethanol, n-propanol, and n-butanol. Sparingly soluble in water, acetone, ethyl acetate, and chloroform. Insoluble in benzene, ethyl ether, and hexane.
(8) Thin layer chromatography (using "Silica Gel 60F$_{254}$" plate supplied by Merck & Co., Inc.):

| Developing solvent | Rf value |
|---|---|
| Chloroform:Methanol (1:1) | 0.34 |

Figure 3:
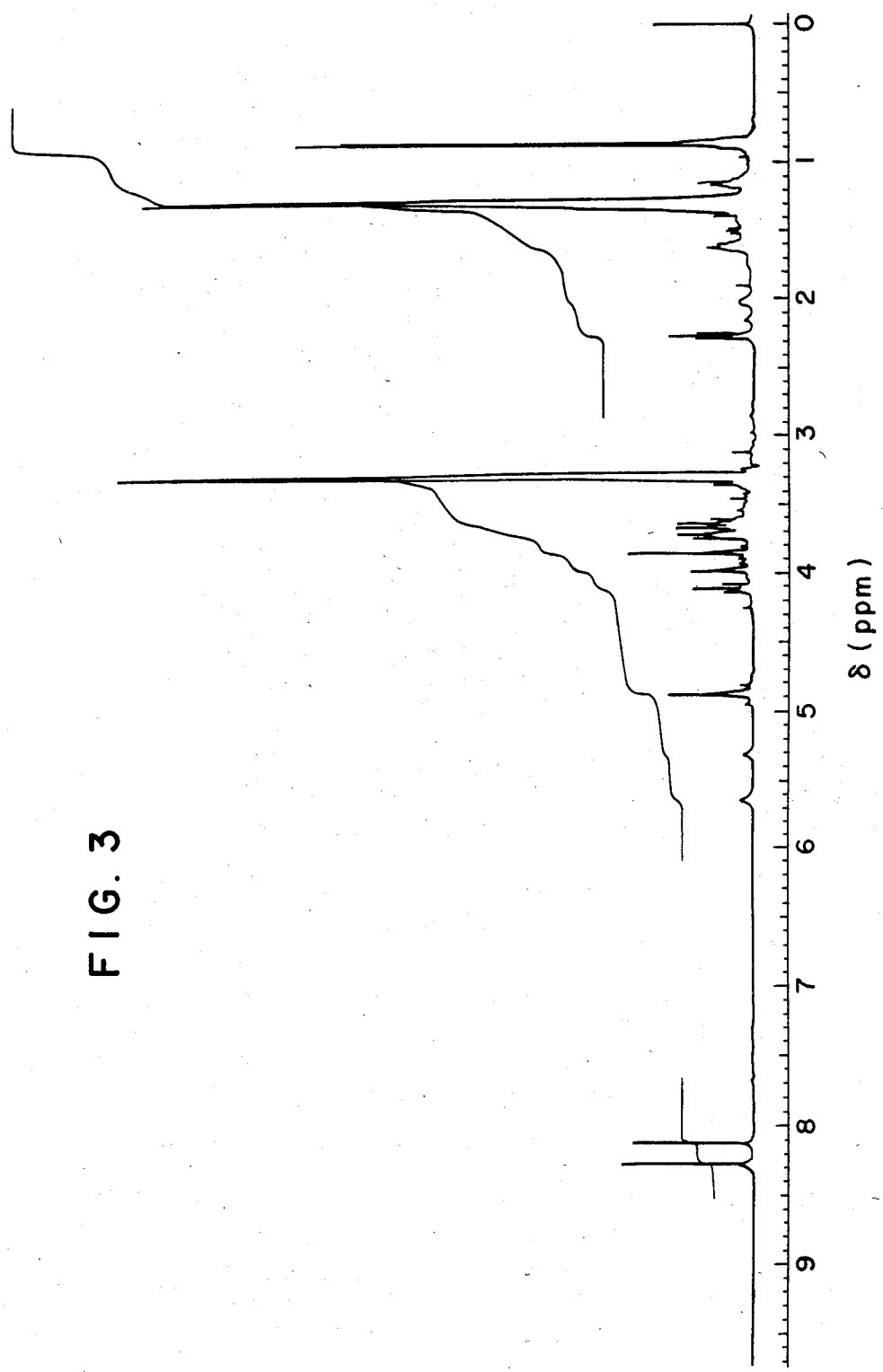
FIG. 3 is the $^1$H-NMR spectrum of Spicamycin.

(9) NMR spectrum (400 MHz, in deuteromethanol): As shown in FIG. 3.

Production of Spicamycin

Outline

The antibiotic, Spicamycin, has been heretofore obtained only by the cultivation of microorganisms. It may be possible, however, to produce this antibiotic by synthetic chemical or microbiological modification of related compounds, or to produce it by total chemical synthesis.

The cultivation technique uses Streptomyces strains capable of producing Spicamycin. More specifically, we have isolated a strain called *Streptomyces alanosinicus* 879-MT$_3$ (H79) and found that this strain produces Spicamycin. Other suitable strains which produce Spicamycin can be isolated from the natural environment by customary methods for use in the isolation of antibiotics-producing microorganisms. It may also be possible to increase Spicamycin production by subjecting Spicamycin-producing microorganisms including *S. alanosinicus* 879-MT$_3$ (H79) to irradiation by radioactive rays or to other treatments.

H79

H79, a Spicamycin-producing Streptomyces strain discovered by us, will be described in detail below.

(1) Origin and Accession No.

H79 is a Streptomyces strain isolated from the soil collected from a flower garden in Ichiki-cho, Hioki-gun, Kagoshima-ken, Japan. This strain was deposited on July 19, 1982 with the Fermentation Research Institute, Agency of Industrial Science and Technology, Ministry of International Trade and Industry of Japan, where it was assigned the accession number FERM P-6636. This strain now bears the accession number FERM BP-449 under the Budapest Treaty on the International Recognition of the Deposit of Microorganism for the Purposes of Patent Procedure.

(2) Mycological characteristics and physiological properties (a) Morphology

Aerial hyphae extend their main axis far, monopodially branching irregularly. The extreme ends of the branches form long spiral spore chains consisting of 10 to 50 or more spores (in the form of coils 20 to 30 μm in diameter, 3 to 6 turns). The spores have spiny surfaces and are of an elliptical shape 0.3 to 0.4 μm in width and 0.5 to 0.7 μm in length. No particular forms such as sclerotia, flagellar spores or sporangia are observed.

(b) Cultural characteristics on various culture media

The cultural characteristics of H79 cultivated at 37° C. were observed in accordance with the "Manual of Method (1941)" adopted by ISP. The results obtained are summarized in Table 1.

(c) Physiological properties and carbon utilization

The physiological properties and carbon utilization of H79 are as set forth respectively in Table 2 and Table 3.

TABLE 1

Cultural Characteristics on Various Culture Media

| Medium | Mass color of the surface of colony | Surface & reverse side pigments of substrate mycelium | Diffusive pigment into medium |
|---|---|---|---|
| Sucrose-nitrate agar | White (a) aerial mycelium develops very slightly | Whitish brown (3ca) Light orange (4ea) | None |
| Glucose-asparagine agar | Velvety, red color series (4ec–5ec) | Light yellow (2fb) Dark yellowish orange (3nc) | None |
| Glycerol-asparagine agar | Powdery aerial mycelium develops slightly, red color series (5ec–5cb) | Pale yellow (2ca) | None |
| Inorganic salts-starch agar | Velvety, red color series (4ec–5ec) | Pale yellow (2ca) Dark yellowish orange (3nc) | None |
| Tyrosine agar | No aerial mycelium develops | Pale yellow (2ca) | None |
| Nutrient agar | No aerial mycelium develops | Whitish brown (3ca) | None |
| Yeast extract-malt extract agar | White (a) aerial mycelium develops very slightly | Light yellow (2ea) | None |
| Oatmeal agar | Powdery aerial mycelium develops slightly, red color series (5eb–5ec) | Light yellow (2fb) | None |

Note:
The color code is in conformity with the Color Harmony Manual, 4th Ed., issued by the Container Corporation of America (1950).

TABLE 2

Physiological Properties

| | |
|---|---|
| Growth temperature range | 20–45° C. |
| Optimum growth temperature | 27–37° C. |
| Liquefaction of gelation | − |
| Hydrolysis of starch | + |
| Coagulation of skim milk | + |
| Peptonization of skim milk | + |
| Production of melanoid pigment | |
| Tyrosine agar | + |
| Peptone-yeast extract-iron agar | + |
| Trypton-yeast extract broth | − |

Note:
+ = positive
− = negative

TABLE 3

Carbon Utilization

| | |
|---|---|
| L-arabinose | + |
| D-xylose | + |
| D-glucose | + |
| D-fructose | + |
| Sucrose | + |
| Inositol | + |
| L-rhamnose | − |
| Raffinose | + |
| D-mannitol | + |

Pridham and Gottlieb basal medium was used.
Note:
+ = positive utilization
− = no utilization (d) Discussion As a result of the observation, 879-MT$_3$ has been identified as an actinomycete of the genus Streptomyces having the characteristic features: (a) the spore chain is in spiral form; (b) the spore has a spiny surface; (c) the aerial mass is of a red color series; (d) the reverse side of the colony has a faint color; (e) the melanoid pigment production is positive; and (f) rhamnose is not utilized as a carbon source. In view of these six basic features examined according to Bergey's Manual of Determinative Bacteriology, 8th Ed. (1974) and the ISP classification, the characteristic features of 879-MT$_3$ are substantially coincident with those of *S. alanosinicus*. As a consequence, this strain has been classified as one of *S. alanosinicus* strains and designated as *Streptomyces alanosinicus*, Thiemann and Beretta, Strain No. 879-MT$_3$.

(3) Cultivation for production of Spicamycin

The antibiotic, Spicamycin, can be prepared by cultivating a Spicamycin-producing Streptomyces strain aerobically in a suitable medium and recovering the object product from the culture.

Culture media may be those containing any nutrient sources which can be utilized by Spicamycin-producing organisms. For example, glucose, sucrose, maltose, starch, oils and fats are useful as carbon sources. Examples of nitrogen sources are organic materials such as soybean meal, cotton seed meal, dry yeast, yeast extract and corn steep liquor, and inorganic materials such as ammonium salts and nitrates, e.g., ammonium sulfate, sodium nitrate and ammonium chloride. If necessary, inorganic salts such as sodium chloride, potassium chloride, phosphates, and salts of heavy metals can also be added. In order to prevent foaming during fermentation, suitable anti-foaming agents such as silicone may be added by a conventional method.

The most suitable method of cultivation is aerobic submerged cultivation which is employed widely for the production of antibiotics. A suitable cultivation temperature is 27° to 37° C., preferably 35° to 37° C. In accordance with this method, the production output of Spicamycin reaches its maximum after 4 to 5 days of shaking cultivation or cultivation under aeration and stirring.

A cultivated broth in which Spicamycin is accumulated can thus be obtained. In the resulting cultivated broth a part of Spicamycin is present in the filtrate of the cultivated broth, while a greater part thereof is present in the mycerial cake.

Spicamycin can be recovered from the cultivated broth by any method suitable for the recovery. One of such methods is based on extraction. For example, Spicamycin in the filtrate of the cultivated broth can be recovered by extraction with a water-immiscible solvent for Spicamycin such as butanol. Spicamycin in the mycerial cake can be recovered by the extraction thereof from the cake, which have been obtained by filtration or centrifugation, with butanol, methanol, ethanol, or acetone. It is also possible to subject the cultivated broth as such to the above-mentioned extraction procedure without preliminary isolation of the mycerial cake. Countercurrent distribution using a suitable solvent may be included in the extraction methods.

Another method for recovering Spicamycin from the cultivated broth is based on adsorption. A Spicamycin-containing liquid material, such as a cultivated broth filtrate or an extract obtained by the extraction procedure described hereinbefore, is subjected, for example, to chromatography using a suitable adsorbent or gel filter, such as column chromatography by the use of silica gel or Sephadex LH20 (supplied by Pharmacia Fine Chemical AB), or high-performance liquid chromatography by the use of Nucleosil $5C_{18}$ (supplied by Nahgel AG). The desired Spicamycin adsorbed onto the adsorbent or gel filter is then eluted therefrom. The resulting Spicamycin solution is concentrated to dryness in vacuo to obtain a crude product of Spicamycin.

The crude Spicamycin product can be purified by carrying out the aforementioned extraction or adsorption procedure, if necessary, in combination, over a necessary number of times. For instance, purification can be accomplished by an appropriate combination of column chromatography using an adsorbent or a gel filter such as silica gel or Sephadex LH20, high-performance liquid chromatography using Nucleosil $5C_{18}$ and the like, and countercurrent distribution. A specific example of the purification method comprises dissolving the crude Spicamycin product in a small quantity of methanol, applying the solution to a column packed with Sephadex LH20, and developing the column with a suitable solvent to elute the active component of Spicamycin. The eluate is concentrated in vacuo and further eluted with methanol by means of high-performance liquid chromatography using Nucleosil $5C_{18}$ to isolate the active fraction. The active fraction thus isolated is concentrated to dryness to obtain a white powder of Spicamycin.

Uses of Spicamycin

The antibiotic, Spicamycin, in accordance with the present invention has carcinostatic activity and antimicrobial activity, and is therefore useful as a medicine.

PHYSIOLOGICAL ACTIVITIES (1) Antitumor activity

Spicamycin exhibits remarkable antitumor activity against leukemia of subject animals. For example, into $CDF_1$ mice were intraperitoneally transplanted P-388 leukemia $1 \times 10^6$ cells/mouse as a suspension, and Spicamycin was administered to the mice for 9 consecutive days from 1 day after the transplantation. The increase of life span (%) compared with the control group consisting of mice administered with physiological saline solution instead of the test compound was calculated by the following equation.

$$\frac{\text{Number of survival days for the test group}}{\text{Number of survival days for the control group}} \times 100 \, (\%)$$

The results were as shown below.

| Dose (mg/kg/day) | Increase of life span T/C (%) |
|---|---|
| 0.125 | 129 |
| 0.25 | 140 |
| 0.5 | 153 |
| 1.0 | 154 |
| 2.0 | 154 (tends to become detrimental) |

(2) Antimicrobial activity

The minimum inhibitory concentration (MIC) of Spicamycin for various microorganisms was determined by the agar dilution method. The results obtained are listed in Table 4 below.

TABLE 4

| Minimum Inhibitory Concentration of Spicamycin | |
|---|---|
| Microorganism | MIC (µg/ml) |
| Bacillus subtilis PCI 219 | >100 |
| Staphylococcus aureus FDA 209P | >100 |
| Micrococcus luteus ATCC 9341 | >100 |
| Pseudomonas aeruginosa NCTC 10490 | >100 |
| Salmonella typhimurium IFO 12529 | >100 |
| Escherichia coli NIHJ JC-2 | >100 |
| Saccharomyces cerevisiae ATCC 9763 | 25 |
| Candida albicans No. Yu 1200 | >100 |
| Candida utilis IFO 0396 | 25 |
| Aspergillus fumigatus IFO 4400 | >100 |
| Penicillium chrysogenum ATCC 10002 | >100 |
| Trichophyton mentagrophytes | 1.56 |

As is apparent from the above data, Spicamycin of the present invention has antimicrobial activity particularly against sycosis-inducing trichophytons, and thus can be used as an antibiotic effective against infections induced by such organisms.

(3) Acute toxicity ($LD_{50}$)

$LD_{50}$ of Spicamycin given by intraperitoneal injection to mice was 40 mg/kg.

(4) Antibiotic

As has been mentioned previously, Spicamycin according to the present invention was found to have antitumor and antimicrobial activities. Accordingly, Spicamycin of this invention can be used as an antitumor or antimicrobial agent.

Spicamycin as an antitumor or antimicrobial agent can be administered via any route suited for the desired purpose in a dosage form determined by the route of administration. Ordinarily, Spicamycin diluted with a pharmaceutically acceptable carrier or dilutent is administered as a drug.

A typical method of administering Spicamycin as an antitumor agent is by injection of its solution in distilled water for injection use or in physiological saline solution. Examples of injection include intraperitoneal injection, subcutaneous injection, intravenous or intraarterial injection, and topical administration in case of animals; and intravenous or intraarterial injection, and topical administration in case of humans.

The doses of Spicamycin are determined in accordance with the results of animal experiments and varying circumstances in such a manner that the total of the doses given continuously or intermittently in each case will not exceed a specific limit. Needless to say, particular doses required vary depending on the mode of administration; situations of patients or animals to be treated, such as age, body weight, sex and susceptibility; food; times of administration; concomitant drugs; and conditions of patients or animals or severity of their diseases. The optimum doses and the frequency of administration under certain conditions must be determined by experts' optimum dose determination tests on the basis of the above-mentioned factors.

EXPERIMENTAL EXAMPLE

In the following example, "%" is "w/v %".

EXAMPLE 1

(1) Preparation of inoculum

A medium used to grow a primary inoculum was prepared by dissolving the following ingredients in 1 liter of water and adjusting the pH of the resultant solution to 7.0.

| | |
|---|---|
| Glucose | 0.4% |
| Malt extract | 1.0% |
| Yeast extract | 0.4% |

15 ml each of the medium thus prepared was sterilized in a large-sized 50-ml test tube and inoculated with a loopful of spores collected from a slant culture of *Streptomyces alanosinicus* 879-MT$_3$. Each lot of the inoculated medium was subjected to shaking cultivation at 37° C. for 48 hours to prepare an inoculum.

(2) Cultivation

A fermentation medium was prepared by dissolving the following ingredients in 1 liter of water and adjusting the pH of the resultant solution to 7.0.

| | |
|---|---|
| Glucose | 2.5% |
| Soy bean meal | 1.5% |
| Dry yeast | 0.2% |
| Calcium carbonate | 0.4% |

100 ml each of the fermentation medium was sterilized in a 500-ml Erlenmeyer flask, and 2 ml of the inoculum prepared as described above was added to each lot of the sterilized medium. Fermentation was carried out at 37° C. on a rotary shaker. After 4 days, the fermentation was terminated, and the mycelial cake separated by filtration was extracted twice with 500 ml of n-butanol. The extract was concentrated to dryness, washed with acetone and water, dissolved in methanol, and passed through a Sephadex LH20 column equilibrated with methanol. The active fraction thus obtained was concentrated to dryness, dissolved in methanol, and subjected to high-performance liquid chromatography using a column (8 mm$\phi \times$250 mm) packed with Nucleosil 5C$_{18}$ under the conditions of methanol as an eluting solvent, a flow rate of 2 ml/min. and a retention time of 5.9 minutes. The fraction whose activity peak was detected by ultraviolet absorption at 264 nm was isolated and concentrated to dryness to yield 80 mg of a white powder of Spicamycin.

What is claimed is:

1. A antibiotic, Spicamycin, having the following physicochemical properties:
   (a) Color and properties: Weakly acidic white powder
   (b) Melting point: 215° to 220° C. (decomposed)
   (c) Specific rotatory power: $[\alpha]_D^{25} = +15°$ (C: 0.15, in methanol)
   (d) Elementary analysis (Found): C: 57.4%, H: 8.38%; N: 15.7%, O: 18.6%
   (e) Ultraviolet absorption spectrum (maximum):

| | |
|---|---|
| CH$_3$OH | 264 nm (E$_{1cm}^{1\%}$ 257) |
| 0.01N NaOH = CH$_3$OH | 272 nm (E$_{cm}^{1\%}$ 226) |
| 0.01N HCl + CH$_3$OH | 273 nm (E$_{cm}^{1\%}$ 258) |

(f) Infrared absorption spectrum (as measured by the potassium bromide method): As shown in FIG. 2,
   (g) Solubility in solvent: Soluble in basic water, dimethyl sulfoxide, methanol, ethanol, n-propanol, an n-butanol Sparingly soluble in water, acetone, ethyl acetate, and chloroform, Insoluble in benzene, ethyl ether, and hexane
   (h) Thin layer chromatography (using "Silica Gel 60F$_{254}$" plate supplied by Merck & Co., Inc.):

| Developing solvent | Rf value |
|---|---|
| Chloroform:Methanol (1:1) | 0.34 |

(i) NMR spectrum (400 MHz, in deuteromethanol): As shown in FIG. 3,
   (j) Chemical formula:

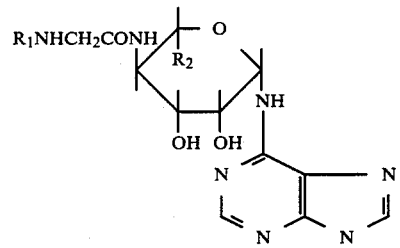

wherein R$_1$ is (CH$_3$)$_2$CH(CH$_2$)$_n$CO wherein n is 8–14, or CH$_3$ (CH$_2$)$_m$CO wherein m is 10–16, and R$_2$ is CH$_2$(OH)CH(OH).

2. A process for producing an antibiotic, spicamycin, which comprises aerobically cultivating *Streptomyces alonosinicus* 879-MT$_3$ (H79) (Ferm BP-449) or derivatives thereof in a suitable culture medium, and recovering from the culture the antibiotic, Spicamycin, having the following physicochemical properties:
   (a) Color and properties: Weakly acidic white powder
   (b) Melting point: 215° to 220° C. (decomposed)
   (c) Specific rotatory power: $[\alpha]_D^{25} = +15°$ (C: 0.15, in methanol)
   (d) Elementary analysis (Found): C: 57.4%, H: 8.3%; N: 15.7%, O: 18.6%
   (e) Ultraviolet absorption spectrum (maximum):

| | |
|---|---|
| CH$_3$OH | 264 nm (E$_{1cm}^{1\%}$ 257) |
| 0.01N NaOH = CH$_3$OH | 272 nm (E$_{cm}^{1\%}$ 226) |
| 0.01N HCl + CH$_3$OH | 273 nm (E$_{cm}^{1\%}$ 258) |

(f) Infrared absorption spectrum (as measured by the potassium bromide method): As shown in FIG. 2,
   (g) Solubility in solvent: Soluble in basic water, dimethyl sulfoxide, methanol, ethanol, n-propanol, and n-butanol Sparingly soluble in water, acetone, ethyl acetate, and chloroform, Insoluble in benzene, ethyl ether, and hexane,
(h) Thin layer chromatography (using "Silica Gel 60F$_{254}$" plate supplied by Merck & Co., Inc.):
| Developing solvent | Rf value |
|---|---|
| Chloroform:Methanol (1:1) | 0.34 |
(i) NMR spectrum (400 MHz, in deuteromethanol): As shown in FIG. 3,
(j) Chemical formula:
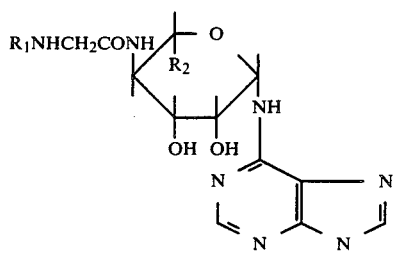
wherein $R_1$ and $R_2$ are as defined in claim 1.
* * * * *